United States Patent
Olivier et al.

(10) Patent No.: US 7,303,280 B2
(45) Date of Patent: Dec. 4, 2007

(54) HIGH-RESOLUTION OPHTHALMIC IMAGING SYSTEM

(75) Inventors: Scot S. Olivier, Livermore, CA (US); Carmen J. Carrano, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 310 days.

(21) Appl. No.: 11/017,384

(22) Filed: Dec. 17, 2004

(65) Prior Publication Data
US 2006/0132709 A1    Jun. 22, 2006

(51) Int. Cl.
*A61B 3/14* (2006.01)

(52) U.S. Cl. .................. 351/206; 351/205; 351/246; 382/243; 382/255; 382/154; 356/364; 356/369

(58) Field of Classification Search .............. 351/206, 351/205, 246; 382/243, 255, 154; 356/364, 356/369; 250/234
See application file for complete search history.

(56) References Cited

U.S. PATENT DOCUMENTS

| | | | |
|---|---|---|---|
| 5,125,730 A * | 6/1992 | Taylor et al. ............... 351/206 |
| 5,448,053 A * | 9/1995 | Rhoads ..................... 250/201.9 |
| 5,734,754 A | 3/1998 | Parker |
| 5,915,048 A | 6/1999 | Hill et al. |
| 6,101,269 A | 8/2000 | Hunter et al. |
| 6,134,009 A | 10/2000 | Zavislan |
| 6,545,265 B1 | 4/2003 | Czarnetzki et al. |
| 6,577,394 B1 | 6/2003 | Zavislan |
| 2004/0005098 A1* | 1/2004 | Carrano et al. ............. 382/254 |

FOREIGN PATENT DOCUMENTS

WO    WO 02/36015 A1    5/2002

OTHER PUBLICATIONS

Miller, D. T., et al., "Bispectral imaging through unknown deterministic aberrations," Journal of Modern Optics, 1995, vol. 42, No. 7, pp. 1523-1546.
Carrano, Carmen J., "Speckle imaging over horizontal paths," Proc. of SPIE, vol. 4825, 2002, pp. 109-120.

* cited by examiner

*Primary Examiner*—Scott J. Sugarman
*Assistant Examiner*—James R Greece
(74) *Attorney, Agent, or Firm*—Eddie E. Scott; John H. Lee

(57) ABSTRACT

A system for providing an improved resolution retina image comprising an imaging camera for capturing a retina image and a computer system operatively connected to the imaging camera, the computer producing short exposures of the retina image and providing speckle processing of the short exposures to provide the improved resolution retina image. The system comprises the steps of capturing a retina image, producing short exposures of the retina image, and speckle processing the short exposures of the retina image to provide the improved resolution retina image.

8 Claims, 3 Drawing Sheets

HIGH-RESOLUTION OPHTHALMIC IMAGING SYSTEM

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to ophthalmic imaging and more particularly to a High-resolution ophthalmic imaging system.

2. State of Technology

U.S. Pat. No. 5,777,719 issued Jul. 7, 1998 to David R. Williams and Junzhong Liang, assigned to the University of Rochester, for a method and apparatus for improving vision and the resolution of retinal images provides the following state of technology information, "A point source produced on the retina of a living eye by a laser beam is reflected from the retina and received at a lenslet array of a Hartmann-Shack wavefront sensor such that each of the lenslets in the lenslet array forms an aerial image of the retinal point source on a CCD camera located adjacent to the lenslet array. The output signal from the CCD camera is acquired by a computer which processes the signal and produces a correction signal which may be used to control a compensating optical or wavefront compensation device such as a deformable mirror. It may also be used to fabricate a contact lens or intraocular lens, or to guide a surgical procedure to correct the aberrations of the eye. Any of these methods could correct aberrations beyond defocus and astigmatism, allowing improved vision and improved imaging of the inside of the eye."

U.S. Pat. No. 6,338,559 issued Jan. 15, 2002 to David R. Williams, Geun-Young Yoon, and Antonio Guirao, assigned to the University of Rochester, for an apparatus and method for improving vision and retinal imaging provides the following state of technology information, "A method for improving the visual performance of a person involves correcting higher-order monochromatic aberrations in combination with the correction of chromatic aberration. Such correction results in a visual benefit greater than that realized by correcting only the higher-order monochromatic aberrations or the chromatic aberration alone. The higher-order monochromatic aberrations are corrected by introducing appropriate phase profiles to compensate for the wavefront aberrations of the eye. This compensation can be provided by contact lenses, IOLs, inlays and onlays having appropriate surface shapes or by corneal shaping achieved through refractive surgery or other techniques. Chromatic aberration can be corrected by spectral filtering or artificial apodization. An apodization filter is described that provides a non-uniform amplitude transmission across the pupil of the eye. Contact lenses or other ocular devices for correcting higher-order monochromatic aberrations may include an appropriate apodization filter for correcting chromatic aberration, or an external optical device for correcting chromatic aberration may be used in combination with a contact lens, etc. for correcting the higher-order monochromatic aberrations."

International Patent Publication No. WO 02/30273 published Apr. 18, 2001 by the University of Rochester, inventors David R. Williams and Antonio Guirao, for determination of ocular refraction from wavefront aberration data provides the following state of technology information, "Ocular refraction is determined from wavefront aberration data, and an optimum customized correction is designed. The eye's wave aberration is measured (202) by using a detector such as a Shack-Hartmann detector (714). From the aberration, an image metric is calculated (214), and the second-order aberrations which optimize that metric are determined (218). From that optimization, the refractive correction (220) required for the eye is determined. The image metric is one of several metrics indicating the quality of the image on the retinal plane or a proxy for such a metric. The required refractive correction (220) can be used to form a lens or to control eye surgery. If it is possible to detect more aberrations than can be corrected, those aberrations are corrected which most affect vision, or for which the eye's error tolerance is lowest."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides an apparatus for providing an improved resolution retina image comprising an imaging camera for capturing a retina image and a computer system operatively connected to the imaging camera, the computer producing short exposures of the retina image and providing speckle processing of the short exposures to provide the improved resolution retina image. The present invention also provides a method of providing an improved resolution retina image comprising the steps of capturing a retina image, producing short exposures of the retina image, and speckle processing the short exposures of the retina image to provide the improved resolution retina image.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
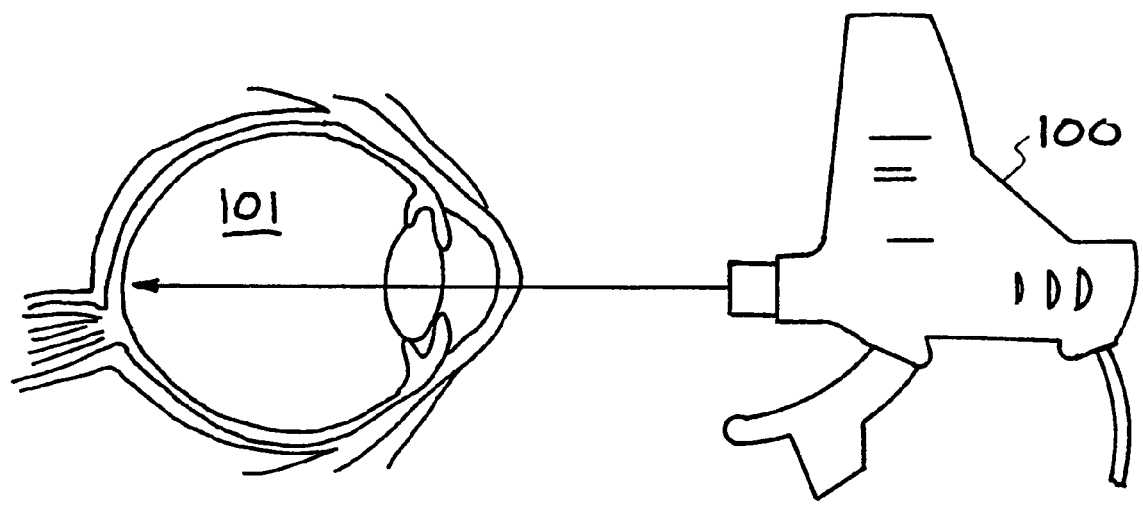
FIG. 1 shows an imaging camera looking into an eye.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to FIG. 1, an imaging camera 100 is shown looking into eye 101. The imaging camera 100 is an imaging camera such as a fundus camera. The imaging camera 100 is used to obtain imagery for high-resolution image processing in accordance with one embodiment of the present invention.

Figure 2:
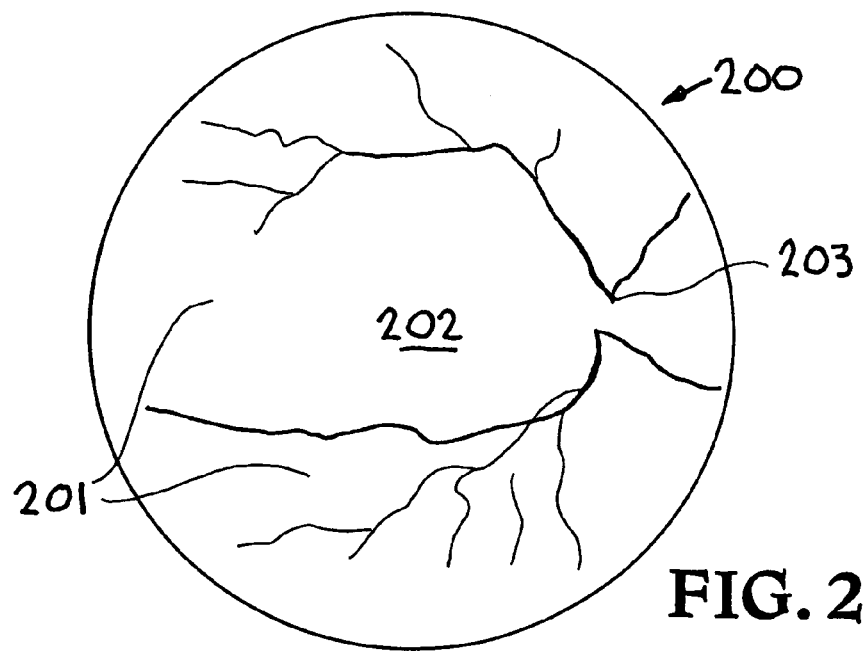
FIG. 2 shows a wide-field, low-resolution image of the retina of the eye.

Referring now to FIG. 2, a wide-field, low-resolution image 200 of the retina of eye 101 is shown. The image 200 shows the peripheral retina 201, the macula 202, and the optic nerve 203.

The present invention provides high-resolution images of internal structures in the eye 101 such as the retina 200. The present invention will allow earlier and more accurate diagnosis of retinal disease and will enable better assessment of treatment protocols. It is understood that aberrations in the optics of the eye degrade image resolution. The present invention provides a method and apparatus for increasing the image resolution to near the diffraction limit of the eye's optics. The image processing involves recording multiple short exposure images. A high-resolution image is then reconstructed using image post-processing. The image processing utilizes a bispectral speckle imaging algorithm.

Figure 3:
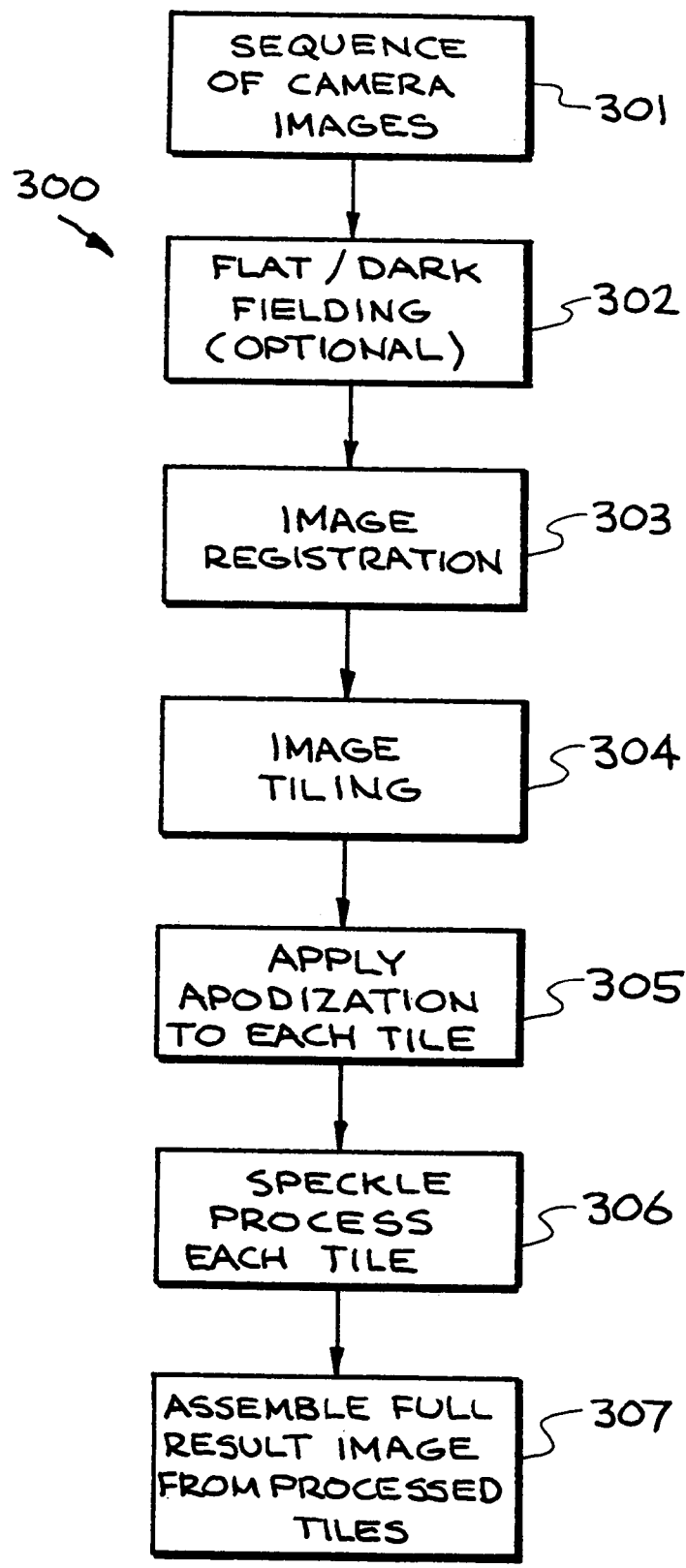
FIG. 3 shows an image processing system.

The image processing consists of acquiring multiple short exposure blurry images which are then processed in a series of processing steps summarized in FIG. 3. The image processing is designated generally by the reference numeral 300. Block 301 represents the sequence of camera images. Block 302 represents flat/dark fielding (this step is optional). Block 303 represents image registration. Block 304 represents image tiling. Block 305 represents apply apodization to each tile. Block 306 represents speckle process each tile. Block 307 represents assemble full results image from processed tiles.

The image is modeled with the following convolutions:

$$i_n(x) = \tau_n(x) * o(x), \quad (1)$$

where $i_n(x)$ is the nth speckle image in an ensemble, $o(x)$ is the object to be recovered, and $\tau_n(x)$ is the combined atmosphere-telescope point-spread function. By a Fourier transform of this relationship, the convolution becomes a multiplication. The powerspectrum is then averaged over each frame and solved for the Fourier magnitude.

$$|o(u)|_{est} \left[ \frac{\langle |I_n(u)|^2 \rangle_n}{\langle |\tau_n u|^2 \rangle_n} \right]^{1/2} \quad (2)$$

Because horizontal path imagery is involved, there is unlikely to be a point reference for generating $\langle |\tau_n(x)|^2 \rangle$. Instead, a model is used for this, where $r_o$, the atmospheric coherence length, is chosen and plugged into the Labeyrie-Korff transfer function. Since $r_o$ is not known, iteration is used to find the best value. Trying values of $r_o$ between 1 cm and 4 cm in increments of 0.5 cm will nearly always yield one or more acceptable images.

For the phase estimate, the complex bispectrum is used. The bispectrum is defined in spatial frequency space as:

$$I_B(u,v) = I_n(u) I_n(V) I_n(-u-v) \quad (3)$$

where u and v are spatial frequency vectors. It is shown that the Fourier phase of the object is recursively related to the phase of the average complex bispectrum according to a three-point integration:

$$arg|O(u+v)| = arg|O(u)| + arg|O(v)| - arg|\langle I_{B,n}(u,v)\rangle_n \quad (4)$$

Starting with aribtrary boundary conditions at the origin and the first two frequency points on axis in the frequency domain, it is possible to recover the object phase through recursive application of Equation 4. In fact, since there are many combinations of u and v that give the same u+v, it is possible to average over large amounts of non-redundant information. The implementation of this recursion allows the selection of how much averaging is performed. Values between 4 and 8 averaged data points give nice results.

After the Fourier magnitude and phase are estimated, they are simply combined and inverse transformed.

In the first step, if needed, is to perform flat fielding of the image sequence. This is needed if there is any dust on the camera optics system that causes noticeable spots in the image. This procedure consists of dividing each frame in the sequence by a flat-field image. A flat-field image can be generated by acquiring one or more frames of a flat field, such as the sky and averaging them together. The image should then be normalized so the average value is one.

In the second step, a global frame-by-frame registration is performed. In the data acquisition, both telescope shaking and atmospheric tip/tilt contribute to x and y shifting of the frames. Shifts are calculated using the standard Fourier correlation methods on high-passed versions of the data. The first frame is taken as the alignment reference, assuming it is a representative frame. It is also possible to align to the frame average just as easily. The shifting is typically less than ten percent of the full image size, which means that the outer pixels of the processed image will be unreliable. If the surveillance system is suitably stabilized, this processing step may or may not be needed.

An intrinsic feature of horizontal-path imaging is that the isoplanatic angles will typically be much smaller than the scene you need to image. As in solar astronomy, Applicants have found that breaking up the image sequence into small regions or tiles can improve the reconstructed image quality substantially. In this processing step, the sequence of large images is split up into a number of smaller overlapped image sequences or image tiles sequences. The amount of overlapping used is 50%. If the size of the tile used is 256×256 pixels, for a 1280×1024 image, it means processing 9×7 or 63 tiles. Applicants have found that the choice of tile size is directly related to the isoplanatic patch size, but can be many times larger to obtain good quality results.

Unlike astronomical scenery, where the object of interest is compact and the data essentially falls away to zero outside the object, horizontal-path terrestrial scenery fills the image. This means that prior to the Fourier transform step of speckle processing, windowing or edge apodization will be needed in order to avoid ringing at the edges. In order to preserve as much of the scene as possible, the choice of window leaves the center of the scene untouched and tapers the edges of the scene. It has been found that a Hanning window taper works well for most cases. The amount of apodization that should be used, which determines the steepness or slope of the window taper, depends on the atmospheric conditions. If the blurring caused by the atmosphere covers N pixels, then the window taper needs to span greater than N pixels. If the taper is too sharp, the speckle processing will confuse the window with the data and put artifacts in the result. It has been found apodization between 50% and 80% works quite well.

After each tile is processed, the full image is assembled. Since the tiles overlap by 50%, a standard square-shaped Hanning window is applied to each reconstructed tile and added up in the proper locations. Hanning windows have the nice feature that when shifted by half a cycle and summed, they add to one. This means there are no artifacts from the overlapping and adding of the tiles.

Figure 4:
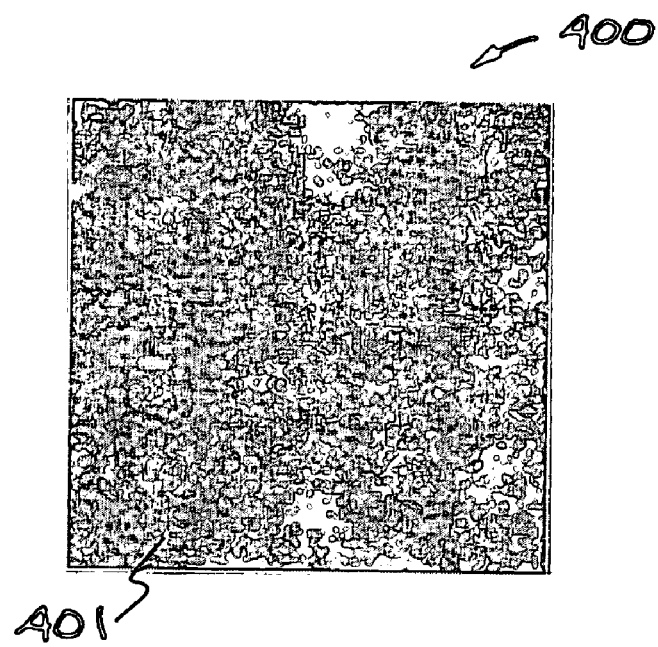
FIG. 4 shows an image produced by zooming into a small region on the retina.

Referring now to FIG. 4, an image 400 is show from zooming into a small region 401 on the retina 200. The image 400 is blurry image. The image 400 can be improved by the present invention.

Figure 5:
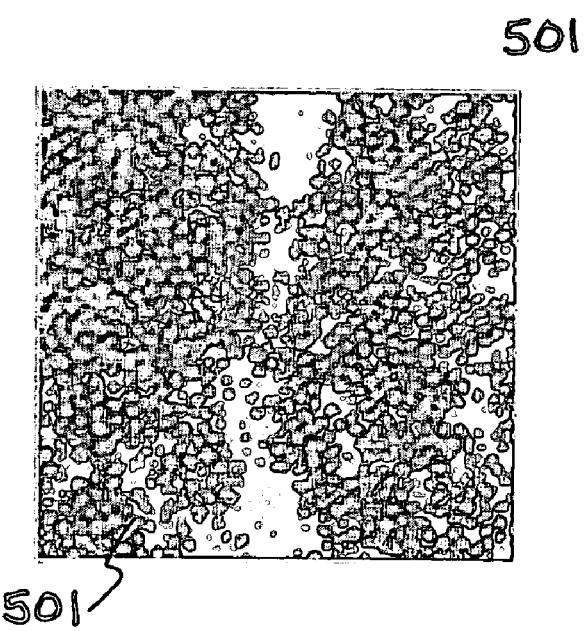
FIG. 5 shows an image produced using the speckle imaging algorithm of the present invention.

Referring now to FIG. 5, an image 500 is shown from zooming into a small region 501 on the retina 200 using the speckle imaging algorithm of the present invention. Using the speckle imaging algorithm of the present invention it is possible to obtain much higher resolution image 500. A comparison of image 400 and image 500 shows that the image 500 has much higher resolution.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for looking into an eye and the retina of the eye and obtaining retina images, the apparatus providing improved resolution retina images, comprising:
   an imaging camera directed to look into the eye for capturing and storing multiple short exposure wide-field, low-resolution retina images of the retina,
   a computer system operatively connected to said imaging camera, said computer system acquiring said multiple short exposure wide-field, low-resolution retina images of the retina, said computer system including
   processor means for image registration of said multiple short exposure wide-field, low-resolution retina images of the retina,
   processor means for image tiling of said multiple short exposure wide-field, low-resolution retina images of the retina producing tiles,
   processor means for applying apodization to said tiles,
   processor means for speckle processing said tiles, and
   processor means for assembling full results images from said tiles to provide the improved resolution of the retina images.

2. The apparatus of claim 1, wherein said computer system acquires said multiple short exposure wide-field, low-resolution retina images of the retina and said multiple short exposure wide-field, low-resolution retina images are multiple short exposure blurry images and wherein said processor means for speckle processing said tiles utilizes speckle processing of said short exposure blurry images to provide the improved resolution retina images.

3. The apparatus of claim 1, including processor means for flat/dark fielding said multiple short exposure wide-field, low-resolution retina images of the retina.

4. An apparatus for looking into an eye and the retina of the eye and obtaining retina images, the apparatus improving resolution of the retina images, comprising:
   a camera, directed to look into the eye and capture and store multiple short exposure wide-field, low-resolution retina images of the retina,
   a processor operatively connected to said camera that acquires said multiple short exposure wide-field, low-resolution retina images of the retina, said processor including
   processor means for image registration of said multiple short exposure wide-field, low-resolution retina images of the retina,
   processor means for image tiling of said multiple short exposure wide-field, low-resolution retina images of the retina producing tiles,
   processor means for applying apodization to said tiles,
   processor means for speckle processing said tiles, and
   processor means for assembling full results images from said tiles to provide the improved resolution of the retina images.

5. The apparatus of claim 4, including processor means for flat/dark fielding said multiple short exposure wide-field, low-resolution retina images of the retina.

6. A method of looking into an eye and the retina of the eye, obtaining images of the retina, and providing improved resolution images of the retina, comprising the steps of:
   using a camera directed to look into the eye for capturing retina images and storing said retina images, said camera producing multiple short exposure wide-field, low-resolution images of the retina,
   using a computer operatively connected to said camera for acquiring said multiple short exposure wide-field, low-resolution images of the retina,
   image registration processing said multiple short exposure wide-field, low-resolution images of the retina,
   image tiling processing said multiple short exposure wide-field, low-resolution images of the retina producing tiles,
   applying apodization to said tiles,
   speckle processing said tiles, and
   assembling full results images from said tiles to provide the improved resolution images of the retina.

7. The method of claim 6, wherein said step of
   using a camera directed to look into the eye for capturing retina images and storing said retina images, said camera producing multiple short exposure wide-field, low-resolution images of the retina includes producing multiple short exposure blurry images and wherein said step of speckle processing said tiles includes speckle processing said short exposure blurry images to provide the improved resolution images of the retina.

8. The method of claim 6, including the step of flat/dark fielding processing said multiple short exposure wide-field, low-resolution images of the retina.

* * * * *